United States Patent [19]

Roberge

[11] 4,126,430
[45] Nov. 21, 1978

[54] PACKED BED TEMPERATURE CONTROL

[75] Inventor: Raymond P. Roberge, Chappaqua, N.Y.

[73] Assignee: Union Carbide Corporation, New York, N.Y.

[21] Appl. No.: 862,128

[22] Filed: Dec. 19, 1977

Related U.S. Application Data

[63] Continuation-in-part of Ser. No. 770,676, Feb. 24, 1977, abandoned.

[51] Int. Cl.² .............................................. B01D 53/04
[52] U.S. Cl. .......................................... 55/20; 55/28; 422/191
[58] Field of Search ............ 23/230 A, 288 R, 288 K; 55/20, 28, 163, 208; 423/219, 659

[56] References Cited

U.S. PATENT DOCUMENTS

| | | | |
|---|---|---|---|
| 3,221,476 | 12/1965 | Meyer | 55/28 |
| 3,261,145 | 7/1966 | Paulson et al. | 55/28 |
| 3,307,921 | 3/1967 | Junginger | 23/288 K |
| 3,592,613 | 7/1971 | Boyd | 23/288 K |
| 3,652,451 | 3/1972 | Boyd | 23/288 K |

OTHER PUBLICATIONS

Eckert et al., Controlling Packed–Column Stills, Chemical Engineering, Mar. 30, 1964.

Primary Examiner—Robert H. Spitzer
Attorney, Agent, or Firm—Saul R. Bresch

[57] ABSTRACT

A process for changing the temperature of a system from one temperature to another where the system comprises at least two packed bed zones operated in series by using combinations of fluids (gases or liquids) and adjusting flow rates and bed masses according to certain prescribed conditions.

5 Claims, 1 Drawing Figure

U.S. Patent
Nov. 21, 1978
4,126,430
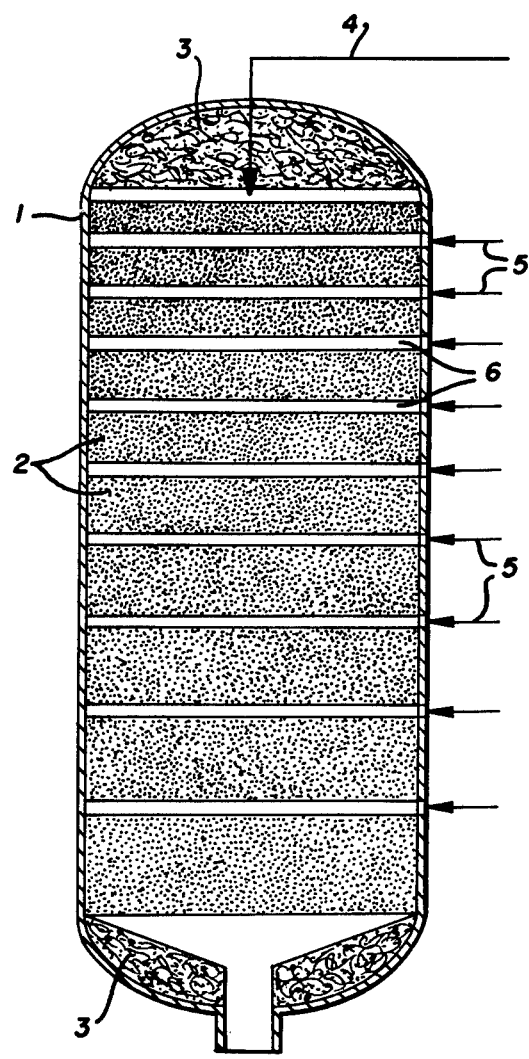

4,126,430

PACKED BED TEMPERATURE CONTROL

This application is a continuation-in-part of Ser. No. 770,676, filed Feb. 24, 1977, now abandoned.

FIELD OF THE INVENTION

This invention relates to a process for controlling the temperature of packed beds operated in series.

DESCRIPTION OF THE PRIOR ART

The packed beds of concern here are conventionally used in sorption-desorption and reaction-regeneration processes where a component of a fluid (defined herein as a material in either the gaseous or liquid state) is absorbed or adsorbed by, or reacts with, the packed bed, i.e., the particulate matter of which the packed bed is made up, and then is released by desorption or regeneration. One such process, that of oxygen separation, is discussed in U.S. Pat. No. 3,980,763, which is incorporated by reference herein. In this patent, particles of a solid solution of praseodymium and cerium oxides make up the packed bed and air is passed through the bed where, under specified conditions, the oxides react with oxygen in the air and are converted to a relatively more oxidized state thus separating the oxygen from the air. Then, the conditions are charged and the particles are regenerated to their original oxidation state releasing the oxygen for ultimate recovery.

In order to operate packed beds on a commercial scale, it is known that the desired process can be carried out in a single packed bed or in several packed beds operated in series. The single packed bed has the advantage of size in that it can be extremely large. Temperature control is conventionally achieved by flowing externally heated or cooled fluids through the bed. The disadvantages of heating or cooling large beds in this manner are that they require high fluid flow rates; exhibit high pressure drops which, in turn, require additional power via compressors or blowers; and suffer from slow cycling. These disadvantages can be offset by the use of multiple packed beds operated in series together with heating and/or cooling devices such as heat exchangers in or between the beds. While heat exchangers, although inefficient, use available heat to advantage, auxiliary heating and cooling cannot be avoided and equipment costs in the multiple bed system are as significant as those in the single bed system to accomplish the same result. Further, each additional piece of equipment adds to the complexity of the system rather than simplifying it.

SUMMARY OF THE INVENTION

An object of this invention, therefore, is to provide an improvement in the temperature control of a series of packed beds whereby equipment and utility (heating, cooling, and power) costs are minimized by a simple, but efficient system and, at the same time, provide a system with the desirable characteristics of reduced flow rates, fast cycling, reduced pressure drop, reduced overall bed mass, and increased mixing of fluids in the beds thus reducing concentration differences in the beds and effluent.

Other objects and advantages will become apparent hereinafter.

According to the present invention, a process has been discovered which is both simple and efficient yet reduces equipment and/or utility costs while providing the mentioned desirable characteristics. It is described as follows:

A process for changing the temperature of a system from temperature $T1$ to temperature $T2$, said system comprising at least two packed bed zones operated in series, each packed bed zone containing
  (i) a packed bed comprised of solid particles; and
  (ii) a mixing zone situated adjacent to the packed bed and associated therewith wherein fluids can be mixed and distributed evenly across a surface of the packed bed comprising the following steps:
  (a) introducing fluid F at temperature $T2$ and at a flow rate $FR1$ into the mixing zone of the first packed bed zone, said flow rate being sufficient to drive fluid F through the packed bed, which packed bed has a mass $M1$ and is initially at a temperature $T1$,
whereby:
  (i) fluid F is driven through the packed bed;
  (ii) the temperature of the packed bed is changed from temperature $T1$ to temperature $T2$; and
  (iii) the temperature of fluid F is changed from temperature $T2$ to temperature $T1$;
  (b) permitting fluid F to exit the first packed bed zone at temperature $T1$;
  (c) introducing fluid F at temperature $T1$ from step (b) into the mixing zone of the packed bed zone immediately succeeding the preceding packed bed zone in the series and, about simultaneously therewith, introducing additional fluid F at temperature $T3$ and flow rate $FR2$ into said mixing zone whereby the fluids are mixed to provide fluid F having a temperature $T2$ and a flow rate $FR3$, said flow rate $FR3$ being sufficient to drive fluid F through the packed bed, which packed bed has a mass $M2$ and is initially at a temperature $T1$,
whereby:
  (i) fluid F is driven through the packed bed;
  (ii) the temperature of the packed bed is changed from temperature $T1$ to temperature $T2$; and
  (iii) the temperature of fluid F is changed from temperature $T2$ to temperature $T1$; and
  (f) permitting fluid F to exit the packed bed zone referred to in step (c)
wherein:
  F is a gas or a mixture of gases, or a liquid or a mixture of liquids;
  $T1$ is the initial absolute temperature of each packed bed;
  $T2$ is the desired final absolute temperature of each packed bed;
  $T3$ is the absolute temperature of additional fluid F;
  $FR1$ is the flow rate of fluid F as introduced into the mixing zone of the first packed bed zone to be determined as follows:

$$FR1 = \frac{M1 \cdot \left[ \int_{T1}^{T2} CPS\, dT + \Delta H \right]}{t\,[CP2 \cdot T2 - CP1 \cdot T1]};$$

$FR2$ is the flow rate of the additional fluid F as introduced into the mixing zone of the packed bed zone referred to in step (c) to be determined as follows:

$$FR2 = A(1 + A)^{j-2} \cdot FR1;$$

FR3 is the flow rate of fluid F after fluid F and additional fluid F are mixed in the mixing zone of the packed bed zone referred to in step (c) to be determined as follows:

$$FR3 = (1 + A)^{j-1} \cdot FR1$$

M1 is the mass of particles in the packed bed of the first packed bed zone to be determined as follows:

$$M1 = \frac{M}{\sum_{j=1}^{N} (1 + A)^{j-1}};$$

M2 is the mass of particles in the packed bed of the packed bed zone referred to in step (c) to be determined as follows:

$$M2 = (1 + A)^{j-1} \cdot M1$$

A is the relationship between heat capacity and temperature to be determined as follows:

$$A = \frac{CP1 \cdot T1 - CP2 \cdot T2}{CP2 \cdot T2 - CP3 \cdot T3};$$

CP1 is the mean heat capacity of fluid F for the temperature range 0 to T1;
CP2 is the mean heat capacity of fluid F for the temperature range 0 to T2;
CP3 is the mean heat capacity of fluid F for the temperature range 0 to T3;
CPS is the heat capacity of the particles in the packed bed;
dT indicates that temperature T is the variable of integration;
$t$ is the time desired for the change of temperature T1 to T2 in each packed bed;
$j$ is an integer which represents the number in the series of the packed bed zone for which the computation is being made, said number to be determined by counting consecutively from, and including, the first packed bed zone;
M is the total mass of particles in all of the packed beds in the system;
N is the total number of packed bed zones in the system; and
ΔH is the heat of reaction or sorption.

It is understood that the relations given above for FR1 and A could alternately be expressed in terms of enthalpies, and also that approximations of these relations could be used whereby heat capacities are assumed to be constant over the temperature ranges of interest.

BRIEF DESCRIPTION OF THE DRAWING

The sole FIGURE of the drawing is a schematic diagram illustrating the side view of apparatus, which can be used to carry out the process of this invention.

DESCRIPTION OF THE PREFERRED EMBODIMENT

The apparatus including the packed beds and the particulate material in the beds used to carry out subject process are conventional. Aside from the apparatus shown in the drawing and described below, it will be understood that piping, fluid inlet and outlet valves, compressors, auxiliary heaters and coolers, other valves, vents, vacuum and other pumps, separators, reservoirs, receiving vessels, and other equipment, all conventional, may be utilized in the system, but will not be described here. Those skilled in the art will also be aware that the packed bed referred to here is also known as a fixed, stationary, or static bed. While the subject process accomplishes its heating or cooling by forced convection, other conventional heating or cooling means may be used to return the beds to their initial temperature where temperature swings are involved.

Referring to the drawing, it will be observed that the illustrated system is made up of ten packed beds 2 surrounded by shell 1. Shell 1 can be metal or a refractory, but in any event it is surrounded by insulation to minimize the transfer of heat into or out of the system. Insulation 3 at the ends and within shell 1 is shown, but the insulation surrounding the shell is not. Each packed bed 2 is considered with the mixing zone 6 directly above it to be a packed bed zone. Mixing zone 6 can simply be a space above the packed bed. The fluid entering the mixing zone comes from the preceding bed, which is just a mass of discrete particles restrained by mesh or other porous material, or through an orifice. Arrow 4 indicates the direction of the initial fluid into the first packed bed zone and the direction of the fluid through the system, and arrow 5 designates the path of additional fluid into mixing zone 6. There are, of course, no heat exchangers in this system since temperature control is achieved through adjustment of flow rates and bed mass. Auxiliary heating or cooling may be used in or around the beds or to heat or cool the initial or additional fluid depending on the temperature swing required for the particular reaction-regeneration or sorption-desorption, which the operator desires to carry out.

It will be understood that the reaction-regeneration or sorption-desorption which have been referred to are merely used to illustrate useful applications of subject temperature control, but the temperature control process is entirely independent of the application and can be used with any packed beds operated in series. It can be used to achieve any one temperature, uniformly, simultaneously, and in a short time. Where another temperature, on the other end of the swing is required, for example, an auxiliary heating or cooling device is used as noted. Examples of the particles in the beds in terms of composition are solid solutions of oxides of praseodymium and cerium, as mentioned above, zeolites, molecular sieves, silica gel, unsupported catalyst, supported catalysts such as silver on an alumina support, and activated charcoal. Conventional packed bed particle sizes are utilized.

The kinds of systems in which this process is useful, in addition to reaction-regeneration and sorption-desorption, are catalytic and heat exchange systems where the particles do not react, absorb, or adsorb.

Although the packed bed zones may be arranged as shown in the drawing with the fluid flowing in a downward direction through the beds (arrow 4), the system can be arranged so that the fluids flow horizontally, at an angle, or upward depending on the fluid and its driving force.

It is apparent that several series of packed beds using subject process can be combined into one system so that, for example, one series of beds will operate at one uniform temperature or with one uniform temperature swing while another series in the same system operate at a different uniform temperature or temperature swing.

In any case, each bed in the series is numbered consecutively beginning with the first packed bed zone where the fluid flowing in the direction of arrow 4 is introduced into the mixing zone. Although this is called a mixing zone for the sake of convenience, mixing does not occur in the mixing zone of the first packed bed zone, the function of the zone being to distribute the fluid evenly across the surface of the bed.

The mixing zone utilized is simply a space above one surface of the packed bed. The flow rates used are sufficient to spread the fluid throughout the space thus distributing the fluid evenly across the packed bed surface and to drive the fluid through the bed. The additional fluid assists in distribution and driving. Other forms of mixing and distribution of fluid may be used.

In sorption-desorption processes, uniform loading is preferred.

The following examples illustrate the invention:

EXAMPLE 1

A reactor having ten packed bed zones as described in the drawing and the specification is loaded with 8 kilograms of Pr - Ce oxide pellets (prepared as described in U.S. Pat. No. 3,980,763) after the beds are sized as set forth below. The objective is to cool the beds from 770° K. to 715° K. in 30 seconds. Air is the cooling fluid. The bulk density of the pellets is 2 grams per cubic centimeter and their mean heat capacity at 715° K. to 770° K. is 0.114 calorie per gram ° K.

Therefore:
F = air
$T_1$ = 770° K.
$T_2$ = 715° K. (air to be introduced into first packed bed zone is externally heated to 715° K.)
$T_3$ = 300° K. (room temperature air is used for additional fluid F)
$FR_1$ = 6.09 grams per second
$FR_2$ =
  0.85 gram per second in bed 2
  0.96 gram per second in bed 3
  1.10 grams per second in bed 4
  1.25 grams per second in bed 5
  1.42 grams per second in bed 6
  1.62 grams per second in bed 7
  1.85 grams per second in bed 8
  2.10 grams per second in bed 9
  2.40 grams per second in bed 10
$FR_3$ =
  6.94 grams per second into bed 2
  7.90 grams per second into bed 3
  9.00 grams per second into bed 4
  10.25 grams per second into bed 5
  11.67 grams per second into bed 6
  13.30 grams per second into bed 7
  15.14 grams per second into bed 8
  17.25 grams per second into bed 9
  19.65 grams per second into bed 10
$M_1$ = 416 grams
$M_2$ =
  474 grams in bed 2
  539 grams in bed 3
  614 grams in bed 4
  700 grams in bed 5
  797 grams in bed 6
  908 grams in bed 7
  1034 grams in bed 8
  1177 grams in bed 9
  1341 grams in bed 10
A = 0.139
$CP_1$ = 0.245 calorie per gram ° K.
$CP_2$ = 0.244 calorie per gram ° K.
$CP_3$ = 0.239 calorie per gram ° K.
$CP_S$ = 0.114 calorie per gram ° K.
t = 30 seconds
M = 8 kilograms
N = 10

Flow rates are regulated by use of manually set needle valves.

Beds are sized as per M1 and M2 above.
Measurements of shell, which is cylindrical:
height = 40 centimeters
diameter = 15 centimeters
Shell is constructed of stainless steel.
Beds are supported by use of the top screen of the succeeding mixing zone.

Temperature in each bed is measured by thermocouples.

It is found that all beds achieve 715° K. ± 20° K. within thirty seconds. Electric heaters (not shown in the drawing) in the beds bring the temperature of the beds to 770° K. at which temperature the oxygen is released by dissociation and the Pr - Ce oxide pellets are regenerated to their lower oxidation state in preparation for the next cycle. Recovery of oxygen is accomplished by conventional methods.

EXAMPLE 2

An adsorber similar to the reactor used in Example 1 is used to remove hydrogen sulfide from natural gas except that only four packed bed zones are used. The adsorbent is 5 Angstrom molecular sieve extruded pellets. The hydrogen sulfide is adsorbed on the packed bed at 300° K. Following adsorption, the bed is regenerated by heating to 560° K. The same procedure is used as in Example 1 except that in this case the invention is used to heat the packed bed from 300° K. to 560° K. in 600 seconds. Methane is used as the regeneration fluid. It is therefore desirable to minimize the flow rate of the regeneration gas because it is a valuable product. The bulk density of the 5A molecular sieve extruded pellets is 0.67 gram per cubic centimeter and their mean heat capacity at 300° K. to 560° K. is 0.23 calorie per gram ° K. The bed is assumed to be uniformly loaded with 3 weight percent hydrogen sulfide and the heat of desorption is 308 calories per gram of hydrogen sulfide desorbed.

Therefore:
F = methane
$T_1$ = 300° K.
$T_2$ = 560° K.
$T_3$ = 1090° K.
$FR_1$ = 3.27 kilograms per second
$FR_2$ =
  1.07 kilograms per second in bed 2
  1.42 kilograms per second in bed 3
  1.89 kilograms per second in bed 4
$FR_3$ =
  4.34 kilograms per second into bed 2
  5.76 kilograms per second into bed 3
  7.65 kilograms per second into bed 4
$M_1$ = 4668 kilograms in bed 1
$M_2$ =
  6195 kilograms in bed 2
  8223 kilograms in bed 3

10914 kilograms in bed 4
A = 0.327
CP1 = 0.500 calorie per gram ° K.
CP2 = 0.563 calorie per gram ° K.
CP3 = 0.753 calorie per gram ° K.
CPS = 0.232 calorie per gram ° K.
t = 600 seconds
M = 30000 kilograms
N = 4

$$\Delta H = \left(308 \frac{\text{calories}}{\text{gram H}_2\text{S}}\right)\left(\frac{0.03 \text{ gram H}_2\text{S}}{\text{gram sieve}}\right) = 9.23 \frac{\text{calories}}{\text{gram sieve}}$$

It is found that all beds achieve 560° K. ± 20° K. within 600 seconds. The beds are then cooled to 300° K. in a conventional manner at which temperature, adsorption of hydrogen sulfide takes place. The methane passes through the system and is recovered by conventional means. The beds are then heated to 560° K. ± 20° K. as aforementioned where desorption of the hydrogen sulfide and regeneration of the molecular sieve pellets takes place. The hydrogen sulfide is also removed by conventional means and the beds are cooled for the next cycle.

EXAMPLE 3

An adsorber similar to the reactor used in Example 1 is used to remove n-butylenes from a stream of isobutylene except that only three packed zones are used. The packed zones are comprised of 5 Angstrom molecular sieve pellets which have been pretreated to lower the polymerization activity of the sieve. During the adsorption step, isobutylene containing 0.4 weight percent n-butylenes is fed to the packed bed at 300° K. until the cumulative isobutylene product contains 0.05 weight percent n-butylenes. Following adsorption the bed is drained and then regenerated by heating to 590° K. The same procedure is used as in Example 1 except that in this case the invention is used to heat the packed bed from 300° K. to 590° K. in 30 minutes. Nitrogen gas is used as the regeneration fluid. It is desirable to minimize the flow of regeneration fluid and to distribute the n-butylenes, which are desorbed in the gas phase, as evenly as possible in the regeneration fluid because this facilitates recovery of the n-butylenes. The bulk density of the 5 Angstrom sieves is 0.67 gram per cubic centimeter and their mean heat capacity at 300° K. to 590° K. is 0.234 calorie per gram ° K. At the beginning of the regeneration step, the bed is assumed to be uniformly loaded with 5 weight percent n-butylenes and the heat of desorption is 178 calories per gram of n-butylenes desorbed.

Therefore:
F = nitrogen
T1 = 300° K.
T2 = 590° K.
T3 = 1260° K.
FR1 = 641 grams nitrogen per second
FR2 =
   254 grams nitrogen per second in bed 2
   355 grams nitrogen per second in bed 3
FR3 =
   895 grams nitrogen per second into bed 2
   1250 grams nitrogen per second into bed 3
M1 = 1058 kilograms 5 Angstrom pellets in bed 1
M2 = 1478 kilograms 5 Angstrom pellets in bed 2
2064 kilograms 5 Angstrom pellets in bed 3
A = 0.396
CP1 = 0.240 calorie per gram ° K.
CP2 = 0.241 calorie per gram ° K.
CP3 = 0.254 calorie per gram ° K.
CPS = 0.234 calorie per gram ° K.
t = 30 minutes
M = 4600 kilograms of 5 Angstrom pellets
N = 3

$$\Delta H = \left(178 \frac{\text{calories}}{\text{gram butylene}}\right)\left(0.05 \frac{\text{gram butylene}}{\text{sieve gram}}\right) = 8.9 \frac{\text{calories}}{\text{sieve gram}}$$

It is found that all beds achieve 590° K. ± 20° K. within 30 minutes. The beds are then cooled to 300° K. in a conventional manner at which temperature adsorption of n-butylenes takes place. The isobutylene passes through the system and is recovered by conventional means. The beds are then heated to 590° K. ± 20° K. as aforementioned where desorption of the n-butylenes in the gas phase takes place. The n-butylenes are also recovered by conventional means and the beds are cooled for the next cycle. The nitrogen gas is heated and recycle to the next regeneration step.

I claim:
1. A process for changing the temperature of a system from temperature T1 to temperature T2, said system comprising at least two packed bed zones operated in series, each packed bed zone containing
(i) a packed bed comprised of solid particles, each particle having a high heat transfer coefficient and a high surface area; and
(ii) a mixing zone situated adjacent to the packed bed and associated therewith wherein fluids can be mixed and distributed evenly across a surface of the packed bed comprising the following steps:
(a) introducing fluid F at temperature T2 and at a flowrate FR1 into the mixing zone of the first packed bed zone, said flow rate being sufficient to drive fluid F through the packed bed, which packed bed has a mass M1 and is initially at a temperature T1,
whereby:
(i) fluid F is driven through the packed bed;
(ii) the temperature of the packed bed is changed from temperature T1 to temperature T2;
and
(iii) the temperature of fluid F is changed from temperature T2 to temperature T1;
(b) permitting fluid F to exit the first packed bed zone at temperature T1;
(c) introducing fluid F at temperature T1 from step (b) into the mixing zone of the packed bed zone immediately succeeding the preceding packed bed zone in the series and, about simultaneously therewith, introducing additional fluid F at temperature T3 and flow rate FR2 into said mixing zone whereby the fluids are mixed to provide fluid F having a temperature T2 and a flow rate FR3, said flow rate FR3 being sufficient to drive fluid F through the packed bed, which packed bed has a mass M2 and is initially at a temperature T1, whereby:
(i) fluid F is driven through the packed bed;

(ii) the temperature of the packed bed is changed from temperature T1 to temperature T2; and (iii) the temperature of fluid F is changed from temperature T2 to temperature T1; and (f) permitting fluid F to exit the packed bed zone referred to in step (c)

wherein:

F is a gas or a mixture of gases, or a liquid or a mixture of liquids;

T1 is the initial absolute temperature of each packed bed;

T2 is the desired final absolute temperature of each packed bed;

T3 is the absolute temperature of additional fluid F;

FR1 is the flow rate of fluid F as introduced into the mixing zone of the first packed bed zone to be determined as follows:

$$FR1 = \frac{M1 \cdot \left[ \int_{T1}^{T2} CPS\, dT + \Delta H \right]}{t\,[CP2 \cdot T2 - CP1 \cdot T1]};$$

FR2 is the flow rate of the additional fluid F as introduced into the mixing zone of the packed bed zone referred to in step (c) to be determined as follows:

$$FR2 = A(1 + A)^{j-2} \cdot FR1;$$

FR3 is the flow rate of fluid F after fluid F and additional fluid F are mixed in the mixing zone of the packed bed zone referred to in step (c) to be determined as follows:

$$FR3 = (1 + A)^{j-1} \cdot FR1$$

M1 is the mass of particles in the packed bed of the first packed bed zone to be determined as follows:

$$M1 = \frac{M}{\sum_{j=1}^{N} (1 + A)^{j-1}};$$

M2 is the mass of particles in the packed bed of the packed bed zone referred to in step (c) to be determined as follows:

$$M2 = (1 + A)^{j-1} \cdot M1$$

A is the relationship between heat capacity and temperature to be determined as follows:

$$A = \frac{CP1 \cdot T1 - CP2 \cdot T2}{CP2 \cdot T2 - CP3 \cdot T3};$$

CP1 is the mean heat capacity of fluid F for the temperature range 0 to T1;
CP2 is the mean heat capacity of fluid F for the temperature range 0 to T2;
CP3 is the mean heat capacity of fluid F for the temperature range 0 to T3;
CPS is the heat capacity of the particles in the packed bed;
dT indicates that temperature T is the variable of integration;
t is the time desired for the change of temperature T1 to T2 in each packed bed;
j is an integer which represents the number in the series of the packed bed zone for which the computation is being made, said number to be determined by counting consecutively from, and including, the first packed bed zone;
M is the total mass of particles in all of the packed beds in the system;
N is the total number of packed bed zones in the system; and
ΔH is the heat of reaction or sorption.

2. The process defined in claim 1 wherein the temperature of each packed bed is changed from temperature T2 back to temperature T1.

3. The process defined in claim 2 wherein the particles remove a component of fluid F at temperature T2 and release the component at temperature T1 and the component is recovered prior to changing the temperature from temperature T1 to temperature T2.

4. The process defined in claim 3 operated in a continuous manner.

5. The process defined in claim 2 operated in a continuous manner.

* * * * *